(12) United States Patent
Patton et al.

(10) Patent No.: US 6,896,655 B2
(45) Date of Patent: *May 24, 2005

(54) SYSTEM AND METHOD FOR CONDITIONING THE PSYCHOLOGICAL STATE OF A SUBJECT USING AN ADAPTIVE AUTOSTEREOSCOPIC DISPLAY

(75) Inventors: David L. Patton, Webster, NY (US); John A. Agostinelli, Rochester, NY (US); James G. Stephens, Pittsford, NY (US); Edward Covannon, Ontario, NY (US)

(73) Assignee: Eastman Kodak Company, Rochester, NY (US)

( * ) Notice: Subject to any disclaimer, the term of this patent is extended or adjusted under 35 U.S.C. 154(b) by 136 days.

This patent is subject to a terminal disclaimer.

(21) Appl. No.: 10/212,342

(22) Filed: Aug. 5, 2002

(65) Prior Publication Data

US 2004/0024287 A1 Feb. 5, 2004

(51) Int. Cl.⁷ .............................. A61B 5/00; A61B 3/02; A61F 2/00
(52) U.S. Cl. .......................... 600/300; 600/26; 351/240
(58) Field of Search .......................... 600/27, 300, 484, 600/545, 425, 418; 434/29, 38, 46, 48, 59, 236; 351/240; 345/419, 8; 473/152; 348/51; 353/7; 128/897, 898

(56) References Cited

U.S. PATENT DOCUMENTS

| | | | |
|---|---|---|---|
| 3,855,998 A | 12/1974 | Hidalgo-Briceno | |
| 4,751,642 A * | 6/1988 | Silva et al. | 473/152 |
| 5,304,112 A * | 4/1994 | Mrklas et al. | 600/27 |
| 5,343,871 A * | 9/1994 | Bittman et al. | 600/545 |
| 5,465,729 A | 11/1995 | Bittman et al. | |
| 5,546,943 A * | 8/1996 | Gould | 600/425 |
| 5,596,994 A | 1/1997 | Bro | |
| 5,742,263 A * | 4/1998 | Wang et al. | 345/8 |
| 5,913,310 A * | 6/1999 | Brown | 128/897 |
| 5,936,663 A * | 8/1999 | Tabata et al. | 348/51 |
| 5,947,908 A * | 9/1999 | Morris | 600/484 |
| 6,012,926 A * | 1/2000 | Hodges et al. | 434/236 |
| 6,034,717 A * | 3/2000 | Dentinger et al. | 348/51 |
| 6,057,846 A * | 5/2000 | Sever, Jr. | 345/419 |
| 6,102,846 A | 8/2000 | Patton et al. | |
| 6,149,586 A | 11/2000 | Elkind | |
| 6,394,963 B1 | 5/2002 | Blazey et al. | |
| 6,416,181 B1 | 7/2002 | Kessler et al. | |
| 6,425,764 B1 * | 7/2002 | Lamson | 434/236 |
| 6,511,182 B1 * | 1/2003 | Agostinelli et al. | 353/7 |
| 2002/0186348 A1 * | 12/2002 | Covannon et al. | 351/240 |

* cited by examiner

*Primary Examiner*—Max F. Hindenburg
*Assistant Examiner*—Nikita R. Veniaminov
(74) *Attorney, Agent, or Firm*—Nelson Adrian Blish

(57) ABSTRACT

An adaptive autostereoscopic display system (10) provides an apparatus for conditioning the psychological state, physiological state, or behavior of a subject (12) by displaying a stereoscopic virtual image at a left viewing pupil (14*l*) and a right viewing pupil (14*r*). A first set of images (100) is displayed and physiological response measurements are obtained from the subject (12). Based on the response of the subject (12) a personalized image response profile is obtained. Then, in order to condition the psychological state, physiological state, or behavior of the subject (12), a second set of images (102), based on the personalized image response profile is displayed.

116 Claims, 8 Drawing Sheets

| IMAGES | ATTRIBUTES |||||||
|---|---|---|---|---|---|---|---|
| | PRIMARY SUBJECT | SECONDARY SUBJECT | TERTIARY SUBJECT | AVERAGE LUMINANCE | DOMINANT HUE | DOMINANT HUE PREVALENCE | SECONDARY HUE | SECONDARY HUE PREVALENCE |
| 1 | MOUNTAINS | WATER | SKY | 28% | BLUE | 24% | GRAY | 8% |
| 2 | WATER | SAILBOAT | SKY | 14% | BLUE | 52% | WHITE | 12% |
| 3 | WHEATFIELD | SKY | MOUNTAINS | 24% | BROWN | 34% | BLUE | 20% |
| 4 | WATER | ROCKS | VEGETATION | 35% | GREEN | 28% | WHITE | 14% |
| 5 | SAND | SKY | WATER | 15% | BROWN | 42% | BLUE | 32% |
| 6 | VEGETATION | BRIDGE | ROCKS | | | | | |
| 7 | | | | | | | | |
| 8 | | | | | | | | |
| 9 | | | | | | | | |
| 10 | | | | | | | | |

FIG. 6

SYSTEM AND METHOD FOR CONDITIONING THE PSYCHOLOGICAL STATE OF A SUBJECT USING AN ADAPTIVE AUTOSTEREOSCOPIC DISPLAY

CROSS REFERENCE TO RELATED APPLICATIONS

Reference is made to commonly-assigned U.S. patent application Ser. No. 09/854,699, filed May 14, 2001, now is a U.S. Pat. No. 6,752,498, entitled ADAPTIVE AUTOSTEREOSCOPIC DISPLAY SYSTEM, by Covannon et al.; U.S. patent application Ser. No. 10/010,500, filed Nov. 13, 2001, now is a U.S. Pat. No. 6,511,182, entitled An AUTOSTEREOSCOPIC OPTICAL APPARATUS USING A SCANNED LINEAR IMAGE SOURCE, by Agostinelli et al.; U.S. patent application Ser. No. 10/095,341, filed Mar. 8, 2002, now is a U.S. Pat. No. 6,702,442, entitled A MONOCENTRIC AUTOSTEREOSCOPIC OPTICAL APPARATUS USING RESONANT FIBER-OPTIC IMAGE GENERATION, by Agostinelli et al.; U.S. patent application Ser. No. 10/101,291, filed Mar. 19, 2002, now is a U.S. Pat. No. 6,550,918, entitled A MONOCENTRIC AUTOSTEREOSCOPIC VIEWING APPARATUS USING RESONANT FIBER-OPTIC IMAGE GENERATION, by Agostinelli et al.; and U.S. patent application Ser. No. 10/137,676, filed May 2, 2002, now is a U.S. Pat. No. 6,768,585, entitled A MONOCENTRIC AUTOSTEREOSCOPIC OPTICAL APPARATUS USING A SCANNED LINEAR ELECTROMECHANICAL MODULATOR, by Agostinelli et al., the disclosures of which are incorporated herein.

FIELD OF THE INVENTION

This invention generally relates to the field of psychological health management and in particular relates to an autostereoscopic display system adapted for psychological health management and to a method for using an autostereoscopic display system for conditioning the psychological state of a subject for biofeedback, stress management, behavior modification, entertainment, and similar applications.

BACKGROUND OF THE INVENTION

The value of image display for conditioning the psychological state, physiological state, or overall behavior of a human subject is widely recognized and documented, with applications in numerous fields. In health-related fields such conditioning can be used for purposes such as stress management as well as for helping in the treatment of conditions such as anxiety, brain injury, or stroke, and other psychological and physiological conditions. In behavioral sciences, such conditioning can be applied to behavior modification, for example. In training applications, conditioning the psychological state, physiological state, or overall behavior of a human subject can be useful in conjunction with simulation systems. In entertainment fields, such conditioning, coupled with careful measurement techniques, could be used to adapt a visual entertainment experience to suit a particular human subject.

For the purpose of this application, it is instructive to clarify the meaning of the verb "condition" as used herein with reference to prior art devices as well as to the present invention. The verb "condition" is broadly defined in the *Merriam-Webster Collegiate Dictionary* as "to adapt, modify, or mold so as to conform to an environing culture" or "to modify so that an act or response previously associated with one stimulus becomes associated with another." Using this sense, the present invention is directed to an apparatus and method for conditioning the psychological state, physiological state, or behavior of a human subject by displaying images to a subject, measuring the subject's response, and adapting further display operation based upon the measured response of the subject. In broadest terms, the present invention is directed to apparatus and methods solutions in health management, stress management, training, and entertainment. It is also instructive to observe that, in the broad sense used in this application, the concept of conditioning the psychological state of a subject encompasses that of modifying the physiological state or the behavioral response of the subject.

An area of particular interest in conditioning the psychological or physiological state of a subject relates to the measurement and management of stress. The measurement and management of a psychological and physiological state, such as the stress, of a subject is a component of a health management program. In order to manage stress, which can have both a psychological and physiological component, it is useful to measure a physiological state of a subject. Useful types of measurements can include measuring galvanic skin response, temperature of fingers, toes, or other extremities, electromyographic (EMG) signals, electroencephalographic (EEG) signals, heart rate, blood pressure, etc., to determine the stress level or level of anxiety of the subject. Dilation of the eye pupil can also be a useful indicator of stress level. The results of these measurements can be converted into signals and fed back as an indication of the subject's level of stress. The subject's level of stress can be determined, measured and compared to a predetermined base level, then converted into sound, light, heat, vibration or images and fed back to the subject.

Several methods for determining a change in stress levels are disclosed in U.S. Pat. No. 6,394,963 and commonly-assigned copending U.S. patent application Ser. No. 09/865,902. The subject in employing stress-reducing techniques uses sound, light, and images to help control stress response. Changes due to physical measures are shown to the subject by a biofeedback device by changing the sound, heat, vibration, light, or images. In the case of images, for example the initial state may show an image out of focus, then, as the stress level decreases, improving focus so that the image becomes more defined. In U.S. Pat. No. 5,465,729, measurements of electro-physiological quantities are used to control a presentation to a subject of a series of pre-stored audio-visual sequences. In this reference, the image does not have to provide feedback and can be used to achieve a relaxed state.

U.S. Pat. No. 3,855,998 shows an entertainment device that includes sensing means connected to the subject. In this reference, the sensing means can, for example, sense the subject's galvanic skin response and, according to the given measured state of the subject, provide a given type of audio-visual stimulation for a timed interval to hold the subject's attention or modify subject response to a desired state. At the end of the interval, the subject's state is again measured and a further timed audio-visual response, based on this measured state, is presented to the subject.

In U.S. Pat. No. 5,596,994, an automated and interactive positive motivation system is disclosed. The system of this arrangement permits a physician, counselor, or trainer to produce and send a series of motivational messages and/or questions to a subject to change or reinforce a specific behavioral response.

U.S. Pat. No. 6,149,586 discloses a system and method for diagnosing executive dysfunctions in patients using virtual reality (VR) technology. However, images shown to the subjects are displayed on a CRT monitor, constraining the capability of the system for achieving full engagement of the subject's attention.

Psychotherapists have found that mental visualization of images or guided imagery is a very effective tool for behavior modification therapy, an important factor in managing a subject's stress. Implementation of guided imagery based therapies can be hindered by variety of factors such as a subject's inability to create and properly control mental images and inability to practice and apply visualization techniques without assistance.

U.S. Pat. No. 6,102,846 discloses a system for managing a psychological and physiological state of a subject using images that are created according to a personalized preferred response profile and specifically tailored to the subject. The image display device disclosed in U.S. Pat. No. 6,102,846 is a high-resolution color monitor. However, as is noted above, display devices of this type are limited in providing realistic images. The subject can be too easily distracted and must exert some effort to become absorbed in the viewing experience with this type of display.

There is considerable interest in applying virtual reality (VR) imaging as part of behavior modification therapy, particularly for treatment of phobias and related neuroses. However, drawbacks with existing VR imaging techniques include cost and complexity, lack of realistic imaging, and an awkward viewing environment due to the need for the subject to wear goggles, headgear, or special glasses.

The potential value of auto stereoscopic display systems is widely appreciated particularly in entertainment and simulation fields. Auto stereoscopic display systems include "immersion" systems, intended to provide a realistic viewing experience for a subject by visually surrounding the subject with a three-dimensional image having a very wide field of view. As differentiated from the more general category of stereoscopic displays, the auto stereoscopic display is characterized by the absence of any requirement for a wearable item of any type, such as goggles, headgear, or special glasses, for example. That is, an auto stereoscopic display attempts to provide "natural" viewing conditions for a subject.

Conventional display systems, such as the type disclosed in U.S. Pat. No. 6,102,846, use a color display monitor or project an image onto a screen for viewing. Optically, this type of image is termed a "real" image, with some form of display surface positioned where the image is formed in space by the optical system. However, for realistic viewing in an immersive imaging system, display of a "virtual" image, as contrasted with a real image, has distinct advantages. A virtual image, formed by an optical system, appears to be more natural in appearance than a real image, with a more lifelike light behavior. A virtual image is not projected onto a surface and therefore does not exhibit screen or monitor artifacts. The virtual image appears to the eye as if it has a spatial position, but this appearance is caused by divergence of light rays rather than by the actual formation of a focused image. A very small source object can provide the scene content for a large virtual image. A display system using a curved mirror and beamsplitter such as is disclosed in U.S. Pat. No. 6,416,181 forms a virtual image that appears to be well behind the curved mirror in space. As a result, vergence and accommodation effects are improved over solutions using real image projection. Vergence refers to the degree at which the observer's eyes must be crossed in order to fuse the separate images of an object within the field of view. Vergence decreases, then vanishes as viewed objects become more distant. Accommodation refers to the requirement that the eye lens of the observer change shape to maintain retinal focus for the object of interest. It is known that there can be a temporary degradation of the observer's depth perception when the observer is exposed for a period of time to mismatched depth cues for vergence and accommodation. It is also known that this negative effect on depth perception can be mitigated when the accommodation cues correspond to distant image position, as can be provided using virtual imaging. In addition to providing an image that is easy for the eye to adapt to, virtual imaging allows a wide field of view.

It must be noted that, because of wide use of the term "virtual reality", there is some confusion of terminology related to virtual images. In some contexts, virtual images are considered to be images that are solely computer-generated. However, for the purposes of the present application, references to "virtual images" refer to images formed optically in the manner described above and differentiated from real images. For the purposes of the present application, virtual image content may be either from natural sources or may be computer-generated. Virtual reality techniques may employ either real images, as is described with reference to U.S. Pat. No. 6,102,846 and U.S. Pat. No. 6,149,586 above, or may employ virtual images.

Pupil imaging also provides advantages for realistic autostereoscopic imaging. In pupil imaging, the eye pupil of the subject is optically conjugate to the projection lens pupil. This allows natural head movement if an eye-tracking and compensation mechanism is employed to adjust the viewing pupil position when the eye pupil is moved. With a system that updates the image display according to the position of left and right viewing pupils, some ability to "look around" an object can be achieved.

An acknowledged design goal for immersion systems is to provide the most realistic viewing environment possible. While this relates most pronouncedly to visual perception, it can also encompass auditory, tactile, and other sensory perception as well. It is well known to those skilled in the virtual reality art that, while the visual display is the primary component needed for an effective immersion experience, there is substantial added value in complementing visual accuracy with reinforcement using other senses of a subject. While the addition of auditory, tactile, and motion stimuli has been implemented for a more realistic and compelling motion picture experience to an audience, there is a need to provide additional sense stimuli in an auto stereoscopic viewing system. Moreover, the use of such additional stimuli may be optimized using sensed feedback information from measurements obtained from a subject.

Thus, it can be seen that, while there have been some conventional approaches for conditioning the psychological and physiological state of a subject using displays that provide real images, there is a need for solutions that provide a more natural and realistic viewing experience. In particular, there would be benefits to providing an improved auto stereoscopic imaging solution for viewing electronically processed images, where the solution provides a structurally simple apparatus, minimizes aberrations and image distortion, and meets demanding requirements for providing wide field of view with large pupil size, for compensating for subject head movement and interocular distance differences, and for providing additional sensory stimulation. At the same time, such a solution could serve as the basis for a system that enables a personalized image response profile to be developed and maintained for conditioning the psychological and physiological state of a subject or for conditioning a subject's behavior.

SUMMARY OF THE INVENTION

It is an object of the present invention to provide an improved autostereoscopic system for conditioning the psychological and physiological state of a subject or for conditioning a subject's behavior. With this object in mind, the present invention provides a system comprising:

(a) an autostereoscopic image display for providing a virtual image to the subject, the virtual image viewable at a right viewing pupil and a left viewing pupil;

(b) at least one feedback sensor for providing a physiological measurement from the subject; and (c) a control logic processor for obtaining the physiological measurement from the at least one feedback sensor, for maintaining a response profile conditioned by the physiological measurement, and for controlling the selection and processing of the virtual image by the autostereoscopic image display based on the response profile.

A feature of the present invention is the use of an adaptive autostereoscopic imaging system for display of images to the subject. In a preferred embodiment, the system forms images using a ball lens that is conjugate to each viewing pupil due to its optical relationship to a curved mirror and a beamsplitter.

A further feature of the present invention is the use of system control logic for maintaining a profile for the subject, where the profile is used as a factor in determining image selection and display.

It is an advantage of the present invention that it provides an improved system and method that can be used for therapeutic use in treatment of a wide variety of psychological and physiological disorders.

It is a further advantage of the present invention that it provides an immersive environment for management and conditioning of the psychological state of the subject. Distractions of external equipment, movement, or personnel are minimized so that the subject can concentrate on visual and other sensory stimuli provided by the system.

The present invention provides for both a system and method for helping to condition or manage the psychological and physiological state of a subject by utilizing images and other stimuli such as sound, smell, etc. In the context of the present invention, the images viewed can be still images, audio-visual images, or video clips, for example. The apparatus and method of the present invention can be part of a personal biofeedback program for managing stress responses or modifying behavior in some way. With the method and apparatus of the present invention, it is possible to overcome the disadvantage of generalized image selection as in conventional arrangements. That is, with the apparatus and method of the present invention, visual and related stimuli are based on personal responses of the subject, rather than on generalized responses obtained from a larger group of subjects. A subject can then utilize these personal images or stimuli using an adaptive autostereoscopic display system along with, or as part of, a biofeedback mechanism for altering the subject's psychological and physiological state, so as to manage and/or reduce stress levels, for example.

The method of the present invention comprises the steps of creating a personalized preferred image response profile for a subject by having the subject view a first set of images and then choose images from the first set of images which provide a preferred response for the subject, wherein the personalized preferred image response profile defines preferred characteristics which are representative of common characteristics of the chosen images; selecting a second set of images from an image library which include characteristics that match the preferred characteristics of the personalized preferred image response profile; and displaying the selected second set of images to the subject to help to manage a psychological and physiological state of the subject.

The present invention further relates to a method of changing, managing or helping a subject to manage a psychological and physiological state using images which comprises the steps of showing a first set of images to the subject; measuring a physiological state of the subject as the subject views the first set of images; and recording images from the first set of images which provide a preferred response based on the measured physiological state of the subject, so as to create a personalized preferred image response profile that defines preferred characteristics which are representative of common characteristics of the recorded preferred images.

The present invention also relates to a system, which changes, manages or helps to manage a psychological and physiological state of a subject using images. The system comprises an image display device which is adapted to store a personalized preferred image response profile for a subject and to store and display a set of images from an image library; and a detector device which measures physiological characteristics of the subject, wherein the physiological characteristics are indicative of a stress level of the subject. The image display device comprises a control mechanism which selects images from the set of images that include attributes that match attributes of the personalized preferred image response profile, and displays the selected images in a desired sequence in accordance with a stress level of the subject as measured by the detection device, to control a stress level of the subject.

The present invention also relates to a method of helping to manage a subject's psychological and physiological state, the method comprising the steps of showing a set of stimuli to the subject; measuring a physiological state of the subject as the subject views the set of stimuli, and making a recording of stimuli from the set of stimuli which provide a preferred response based on the measured physiological state of the subject, so as to create a personalized preferred response profile that defines preferred characteristics which are representative of common characteristics of the recorded stimuli.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

FIG. 6 is a chart illustrating an example of a comparison of images and attributes which can be utilized with the system of the present invention;

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Figure 1:
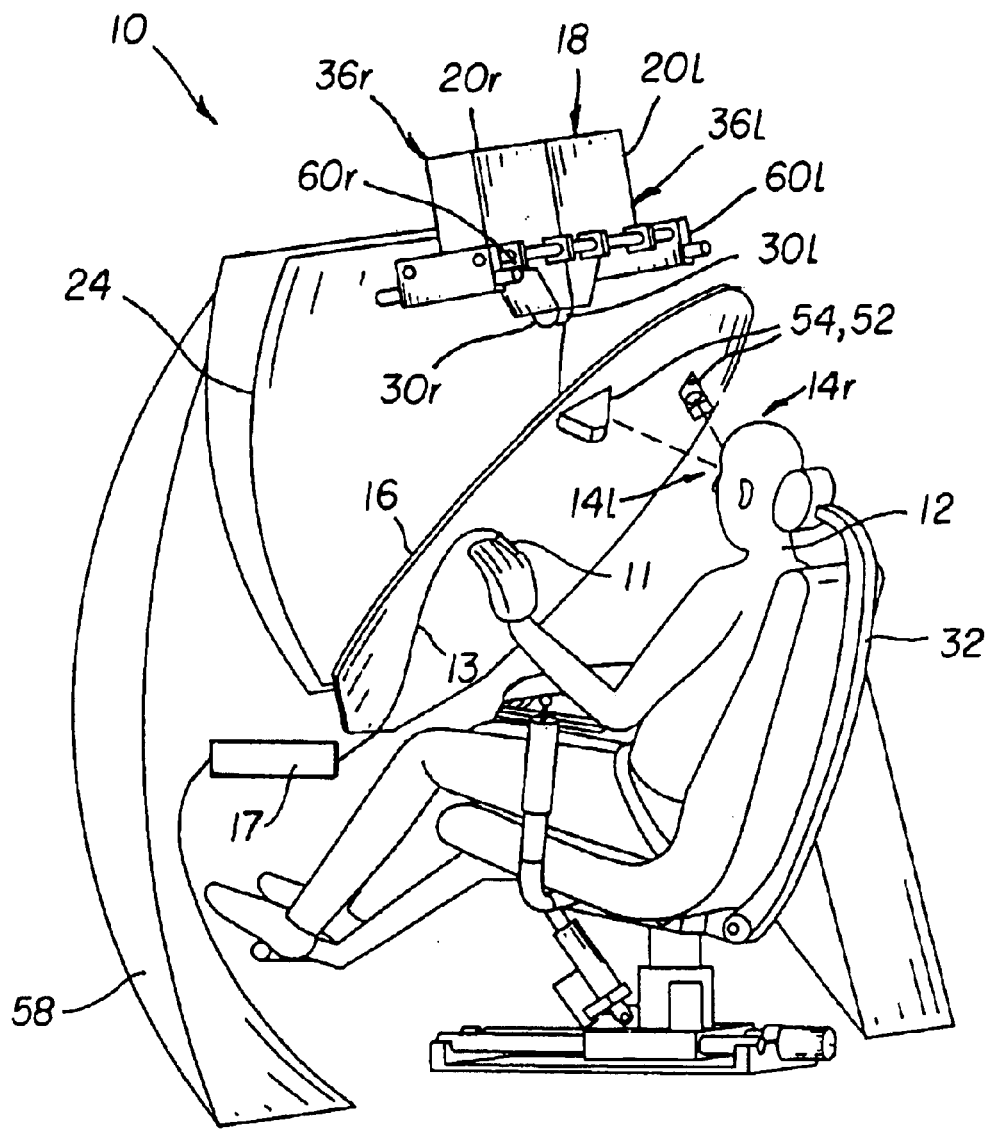
FIG. 1 is a perspective view showing major components of an adaptive autostereoscopic imaging system of the present invention.

Referring to FIG. 1, there is shown an adaptive autostereoscopic display system 10, arranged as a biofeedback imaging apparatus. Adaptive autostereoscopic display system 10 can be used to monitor, condition, and manage the psychological and physiological state of a subject 12, either controlled by another person, such as a medical professional, or programmed for control by subject 12. Although the present invention will be primarily described as using images for behavior modification such as stress management, it is recognized that other sensory stimuli such as sound, smell, touch, for example, can be provided to subject 12 within the context of the present invention. Within this detailed description, it must be emphasized that the broad definitions for the terms "conditioning" and "psychological state," given in the Background section of this application, apply to the present invention.

Detailed description of the optical subsystem of adaptive autostereoscopic display system 10 is given in commonly-assigned copending U.S. patent Ser. No. 09/854,699. In the preferred embodiment, adaptive autostereoscopic display system 10 provides virtual autostereoscopic images at left and right viewing pupils 14l and 14r. Left and right viewing pupil forming apparatus 36l and 36r each project images through a left and right ball lens assembly 30l and 30r onto a beamsplitter 16. Beamsplitter 16 interacts with a curved mirror 24 to form a virtual image for each viewing pupil 14l and 14r. Within left and right viewing pupil forming apparatus 36l and 36r, images can be generated using a spatial light modulator such as a liquid crystal device (LCD) or a digital micromirror device (DMD), for example. Alternately, images could be generated by one or more lasers, using a grating light valve or similar electromechanical device, or using an OLED.

As illustrated in FIG. 1, subject 12 is seated in an adjustable chair 32 for viewing an image projected by an autostereoscopic image delivery system 18 to left viewing pupil 14l and to right viewing pupil 14r. Autostereoscopic image delivery system 18 comprises left viewing pupil forming apparatus 36l for forming and positioning left viewing pupil 14l and right viewing pupil forming apparatus 36r for forming and positioning right viewing pupil 14r. A housing 58 provides a structure for mounting the various components of auto stereoscopic image delivery system 18 and related components.

Figure 2:
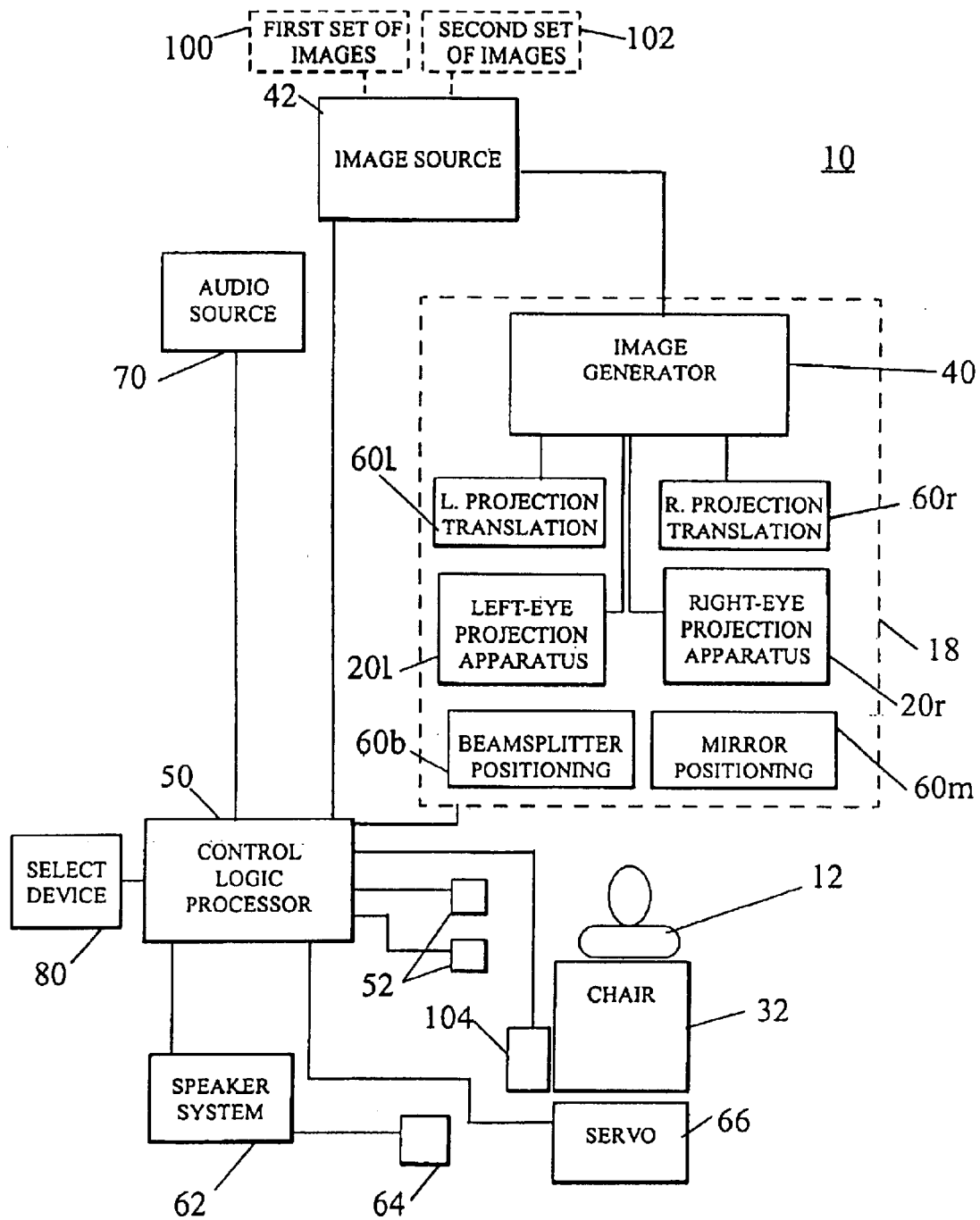
FIG. 2 is a block diagram showing key image forming, control logic, stimulus and feedback components of the system of the present invention.

Referring to FIG. 2, there is shown a schematic block diagram with key control and signal paths for major components of adaptive autostereoscopic display system 10. An image source 42 provides image content to an image generator 40, part of autostereoscopic image delivery system 18. Image generator 40, comprising a digital image modifying device under the control of a control logic processor 50, then cooperates with left and right eye projection apparatus 20l and 20r and viewing pupil forming apparatus 36l and 36r (FIG. 1) to provide stereoscopic virtual images at left and right viewing pupils 14l and 14r.

Image source 42 may provide any of a number of types of images, such as, but not limited to, the following:

(a) Live images from cameras locally or remotely positioned.

(b) Images from film, such as conventional motion picture images.

(c) Images processed digitally, such as digital cinema images for example. This can include images stored on a storage medium, such as a computer hard disk or removable storage device, for example.

(d) Images generated digitally, such as computer simulations. This can include images stored on a storage medium, such as a computer hard disk or removable storage device, for example.

From the description of FIGS. 1 and 2, it can be observed that similar optical components within autostereoscopic image delivery system 18 are used to present separate left and right images to each eye of subject 12. When the description that follows applies in general to either left- or right-components, appended "l" and "r" designators are omitted unless otherwise needed.

Referring again to FIGS. 1 and 2, control logic processor 50 controls the operation of image generator 40, the position of projection apparatus 20, and the overall operation of a projection translation apparatus 60 within auto stereoscopic image delivery system 18. A beamsplitter positioning apparatus 60b and a mirror positioning apparatus 60m would enable adaptive autostereoscopic display system 10 to adapt to changes in position of subject 12 as well as to changes in height, head position, and the like. Control logic processor 50 may also control a chair servo mechanism 66 or movable platform and can accept feedback data about subject 12 from subject feedback sensors 52 such as cameras 54 or other devices, such as photosensors, for example. A manual feedback control 104 provides an alternate means for obtaining instructions from subject 12.

Adaptive autostereoscopic display system 10 could be equipped with a feedback control loop for sensing and responding to a position or gesture of subject 12. For example, as is described in commonly-assigned copending U.S. patent application Ser. No. 09/854,699, adaptive autostereoscopic display system 10 could be equipped to sense and compensate for an interocular distance or a gesture of subject 12 or could use speech recognition as a sensed input. In addition, adaptive autostereoscopic display system 10 could be designed to provide some measure of compensation for parallax error or "see-around" capability, adjusting left and right eye images based on eye positions observed for subject 12.

Control logic processor 50 may also control other optional output devices for controlling vibration, temperature, fans, or other devices. Tactile output could be provided, such as by means of a glove (not shown) or by one or more fans or other devices. These tactile devices could also control temperature, such as the temperature of air from a fan outlet, for example. An olfactory output apparatus (not shown) could be employed as an output device for emitting an odor perceptible to subject 12. Optional audio content from an audio source 70, also under control of control logic processor 50, can be directed to a speaker system 62 and to one or more speakers 64. Control logic processor 50 is a computer of some type, possibly comprising a dedicated CPU or microprocessor, programmed to generate output commands based on program instructions and conditioned by sensed input feedback data. For example, FIG. 1 shows a detector device 11 which can be operationally associated as a feedback source with adaptive autostereoscopic display system 10. Detector device 11 can be a measuring or monitoring apparatus for obtaining feedback data from subject 12, such as galvanic skin response, temperature of fingers or other extremities, blood pressure, pulse rate, breathing, eye movements, or other functions that indicate the level of stress or other condition of subject 12. Detector device 11 can be a device attached to the body in a non-invasive manner, could be an instrumented glove or other device that is easily worn, could be a manipulable device, or could be a non-contact sensing device, such as an optical monitor for measuring pupil dilation, for example. An interconnect cable 13 or other suitable interface mechanism connects detector device 11 with a control mechanism 17. Control mechanism 17 may be programmed to interact with detector device 11 and cause adaptive autostereoscopic display system 10 to display a preferred image based on the measured physiological characteristics or level of stress of subject 12.

For example, control mechanism 17 can detect changes in stress related physiological functions of subject 12 and trigger a change in the sequence or type of images displayed by adaptive autostereoscopic display system 10. More specifically, control mechanism 17 can include software that is designed to select images from a first set of images 100 or from a second set of images 102 supplied by image source 42, where the selected set 100 or 102 is compatible with attributes defined by a personalized preferred image response profile for subject 12. Adaptive autostereoscopic display system 10 would then display the selected images in a desired sequence in accordance with the stress level of subject 12 as measured by detection device 11, to help manage stress, for example.

First set of images 100 may be representative of a personalized preferred image response profile for subject 12, the details of which will be described later. First set of images 100 can be tailored to information obtained from subject 12 and can include a series of images based on a variety of themes (such as ocean, forest, desert, sunset, or similar themes, for example.) Alternately, first set of images 100 may include personal images of subject 12, such as family and friends, for example. Images in first or second set of images 100 or 102 can be arranged in a preset sequence, such as from chaotic, to ordered, to placid, as might be useful for helping to modify behavior and reduce stress, for example. Adaptive autostereoscopic display system 10 can further be adapted to store for display, in image source 42, second set of images 102 from an image library or from personal images of subject 12. As previously discussed, the stored images can be of any type, such as still images, audio-visual images, video clips, or computer-generated images, for example.

Creating a Personalized Preferred Image Response Profile

The process of creating a personalized preferred image response profile for determining first set of images 100 for each subject 12 will now be described. The personalized preferred image response profile is created by having subject 12 view a wide variety of images and measuring physiological effects on subject 12 as an indicator of psychological state. The measurements can be made using observer feedback sensor 52, camera 54, or detector device 11. Measurements could record one or more physiological symptoms, such as, but not limited to EMG, EEG, galvanic skin response, skin temperature, heart rate, blood pressure, eye movement, or pupil dilation, for example. The measurements obtained are correlated to the corresponding image or image sequence viewed by subject 12 at the time. The measured results indicate how subject 12 reacts to a specific image or to a sequence of images. From this data, a personalized preferred image response profile is created for subject 12. In practice, first set of images 100 will generally be images that provide a preferred response for the type of behavior modification desired, such as lowering a stress level. In this way, the personalized preferred image response profile can include data from first set of images 100 which is representative of common characteristics, or attributes of first set of images 100 that tend to provide a preferred response to the individual. The personalized preferred image response profile can then be used to select images from an image library which includes second set of images 102. The selected images can be used by as personal biofeedback images by subject 12. Thus, by using the personalized preferred image response profile, images are selected that have a desired effect for subject 12. More generally, the personalized preferred image response profile may be comprised of a set of information that describes the selected images and others that match the response profile.

As an example, to create a personalized preferred image response profile, subject 12 accesses an image library stored in image source 42 and keys in a code that links to the personalized preferred image response profile specific to subject 12. This personalized preferred image response profile is then used by the image library to select images from the image library. These selected images are displayed so that subject 12 can choose a desired set. This selected set can then be loaded as second set of images 102, for example. The personalized image response profile allows subject 12 to pick from a variety of categories such as seascapes, desert scenes, forest scenes or personal images such as from home, garden, favorite museum, pets, or other images, for example. This allows subject 12 to change the images that are used as biofeedback, reducing the risk that displayed images within second set of images 102 will have an adverse effect on the psychological state of subject 12.

Once a personalized preferred image response profile is set up, subject 12 interacts with detecting device 11 and loads the selected images from second set of images 102 for display by adaptive autostereoscopic display system 10. The output from detecting device 11 feeds into control mechanism 17 over interconnect cable 13 or over some other type of wireless interface. Subject 12 can set a base state by recording measured levels of stress, using measurements of symptoms such as EMG, EEG, galvanic skin response, skin temperature, heart rate, blood pressure, eye movement, and the like. An image from the selected images of second set of images 102 which relates to this level of stress can them be displayed on adaptive autostereoscopic display system 10. At this point, subject 12 can begin a personal stress reduction regime and determine the changing level of stress is manifested with the transition in images. For example, as the stress level decreases, the images displayed to subject 12 could change from a chaotic state to a serene state. In another arrangement, the image transition may be from a first image to a second image, where the second image is very unlike the first image, with a corresponding measurement made of the change in stress symptoms for subject 12, on the basis of the personalized preferred image response profile. Image classification may be based on resolution, color, contrast, scene content, or other characteristic.

Figure 3:
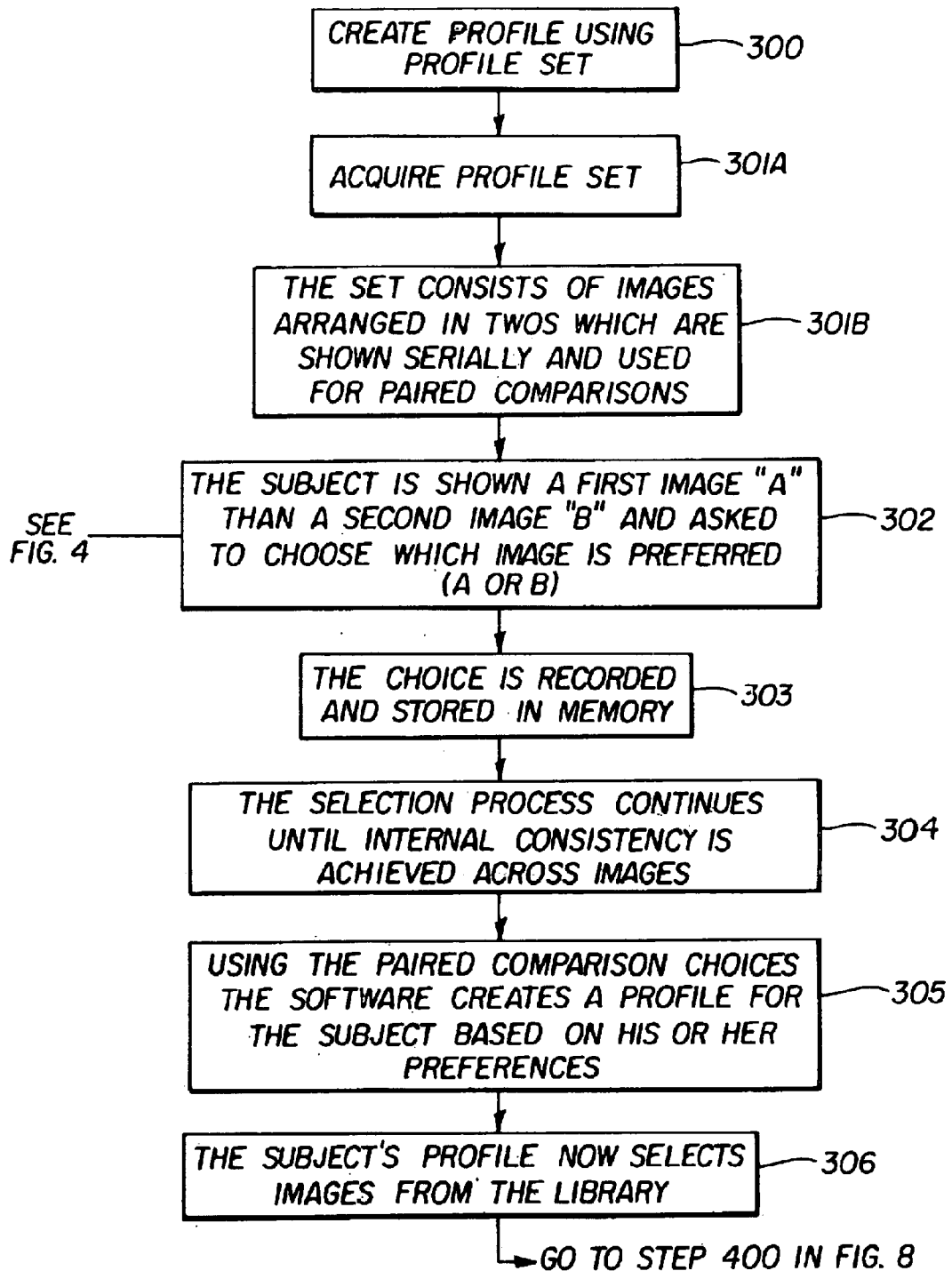
FIG. 3 is a flow chart giving process steps for the present invention.
Figure 4:
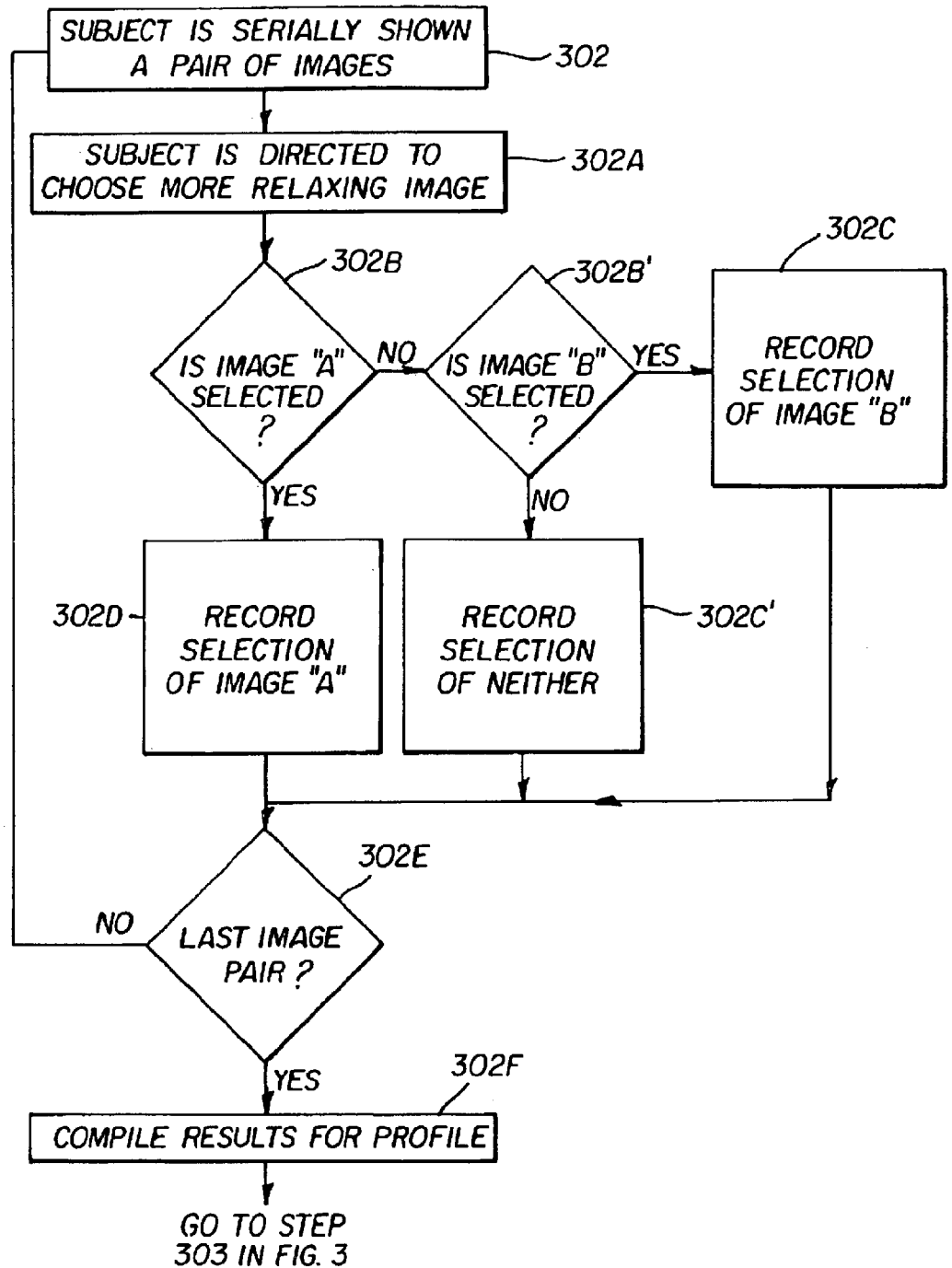
FIG. 4 is a further flow chart showing a comparison of images, which can be utilized within the system of the present invention.
Figure 5:
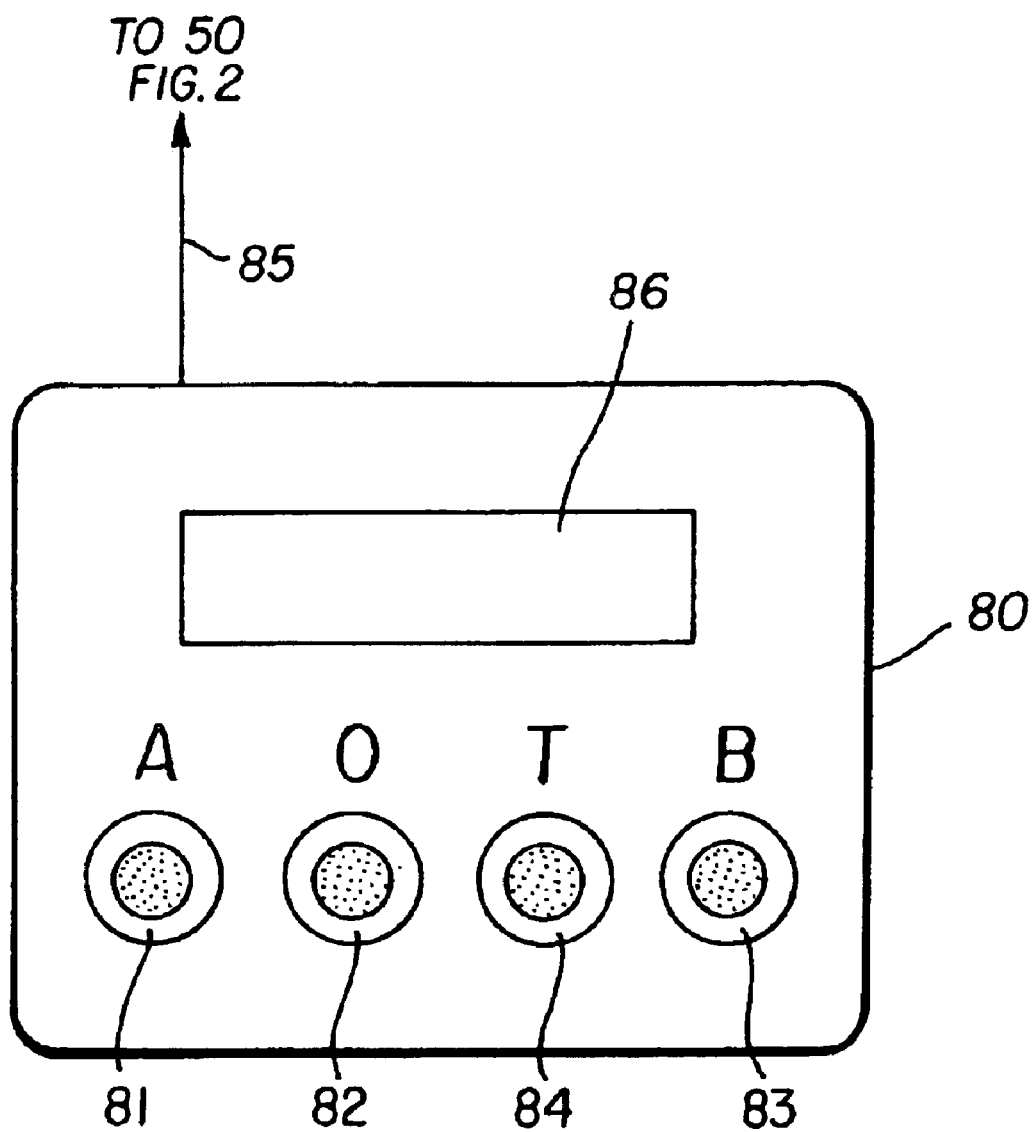
FIG. 5 is an example of a selector device, which can be used for paired comparisons of images.

Referring now to FIG. 3, subject 12 creates a profile using a profile set in an initial step 300. Subject 12 then obtains an image profile set (step 301A). As illustrated in step 301B, the profile set can include images arranged in a series of twos which are used for paired comparisons. Subject 12 is then shown the first of the two images and then the second of the two images and asked to chose a preferred image (step 302). FIG. 4 illustrates a flow chart with respect to the comparison of images of step 302, while FIG. 5 illustrates a selector device 80, connected to the system of the present invention, that can be used by subject 12 to choose, compare and select images. As shown in FIG. 5, selector device 80 includes selector buttons 81, 82, 83, and 84. Selector button 81 corresponds to image A and is activated or depressed by subject 12 when image A provides a preferred response when compared to image B. Selector button 83 corresponds to image B and is activated or depressed by subject 12 when image B provides the preferred response when compared to image A. Selector button 82 can be activated or depressed by subject 12 when no image is preferred. Selector button 84 is used to toggle between images A and image B. Selector device 80 is connected via a connector 85 to control logic processor 50 (FIG. 2) which records and stores the selections made by subject 12. Selector device 80 also connects to image source 42 and image generator 40 via control logic processor 50. Selector device 80 has a display panel 86 to indicate to subject 12 which image in the sequence is being displayed.

As noted in FIG. 4, after subject 12 is shown a pair of images (step 302), subject 12 is then directed to choose the more relaxing image (step 302A). In step 302A, subject 12 can provide a direct response with respect to the preferred images by activating or pressing one of selector buttons 81–83 of selector device 80. As an alternative, preferred images can be automatically chosen based on a physiological measurement obtained from subject 12 by detecting device 11 as illustrated in FIG. 1.

Referring again to FIG. 4, after step 302A, there is a check to see if an image "A" is selected (step 302B). If the answer to step 302B is no, there is a check to see if image "B" is selected (step 302B'). If the answer to step 302B' is yes, the selection of image "B" is recorded (step 302C). If the answer to step 302B' is no, then there is a recording that neither image has been selected (step 302C'). If the answer to step 302B is yes, there is a recording of the selection of image "A" (step 302D). After either of steps 302C, 302C' or 302D, there is a check to see if the image pair shown to subject 12 is the last image pair (step 302E). If the answer to step 302E is no, then above steps are continued as noted in the flow chart of FIG. 4 until the last image pair is chosen and the complete selection of images is noted by subject 12. After step 302E, the process proceeds to compile the results of the images chosen by subject 12 (step 302F).

Referring back to FIG. 3, the chosen images or choices are thereafter recorded and stored in memory (step 303). At this point, the selection process could be continued until internal consistencies are achieved across images (step 304). For example, and with reference to FIG. 6, each of the images in the profile set can have certain attributes or characteristics. FIG. 6 shows a chart of sample images and their attributes. In viewing the images selected by subject 12, predominant attributes or characteristics of the selected images could be determined and these attributes or characteristics utilized to help create the personalized preferred image response profile for subject 12. Also, a search can be initiated using these attributes or characteristics as described in, for example U.S. Pat. No. 6,102,846, the subject matter of which is incorporated by reference. In step 305, the selection results of the paired comparisons, as well as the assessment of the attributes of the chosen images or sequence of the images, provides a basis for creating a personalized preferred image response profile for subject 12 based on exhibited preferences. The personalized preferred image response profile for subject 12 can now be used to select second set of images 102 from an image library as noted in step 306 or from personal images of subject 12. At the conclusion of step 306, the process goes to step 400 in FIG. 8.

Figure 8:
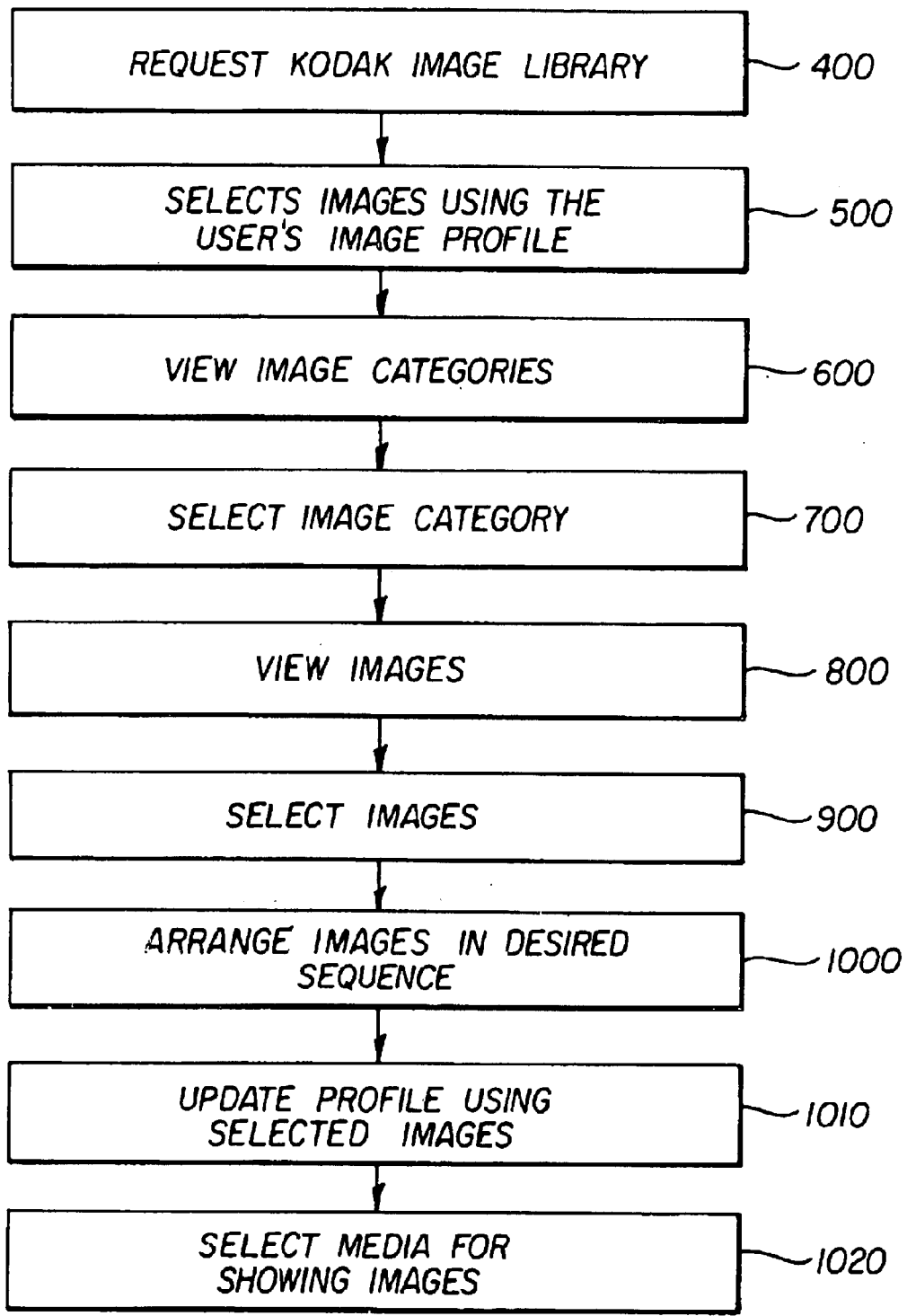
FIG. 8 is a flow chart showing image selection.

Referring to FIG. 8, there is shown the next stage in this process, whereby subject 12 can use adaptive autostereoscopic display system 10 as illustrated in FIG. 1 with an image library including second set of images 102. In step 500, images from second set of images 102 using the personalized preferred image response profile are selected and viewed in categories (step 600). Thereafter, subject 12 can select image categories (step 700), view the images (step 800), select images (step 900) based on the personalized preferred image response profile, and arrange the images in a desired sequence for achieving stress reduction (step 1000) (not shown). As a further option, a computer program can be utilized to update the profile for subject 12 using data from the newly selected images (step 1010) (not shown) and the media for showing the images can be selected (step 1020) (not shown).

The images obtained by the image source 42 can be in the form of a video, photo CDs, CD ROMs, floppy disks, DVD, lenticular imaging, downloaded or EEPROM.

With the process of the present invention, subject 12 creates a personalized preferred image response profile by viewing a first set of images on the adaptive autostereoscopic display system 10 such as from a profile set that includes images arranged in pairs, and compares and chooses images from the first set of images, which provide a preferred response for subject 12. In making the comparison choices between images as illustrated in the flow charts of FIGS. 3 and 4, those images which provide a preferred behavior such as the stress response level for subject 12 are chosen or are automatically selected based on measured stress levels of subject 12. Selected images from this comparison are used to create a profile for subject 12 based on personal preferences. Thus, the personalized preferred image response profile will define preferred characteristics that can be representative of common characteristics of the chosen images. Subject 12 can then select a second set of images from an image library, where the images have characteristics that match the preferred characteristics of the personalized preferred image response profile.

Having created the personalized preferred image response profile, which is then stored in the image source 42, adaptive autostereoscopic display system 10, using detector device 11 as illustrated in FIG. 1, can be used to measure the present stress level of subject 12. Based on the personalized preferred image response profile, adaptive autostereoscopic display system 10 can display selected images from the image library to subject 12 in a sequence chosen by subject 12, in accordance with the measured stress level, to enable subject 12 to manage and/or control this stress level. Subject 12 can be shown scenes known to induce stress and be taught, using biofeedback techniques, to control response to the images, for example.

Figure 7:
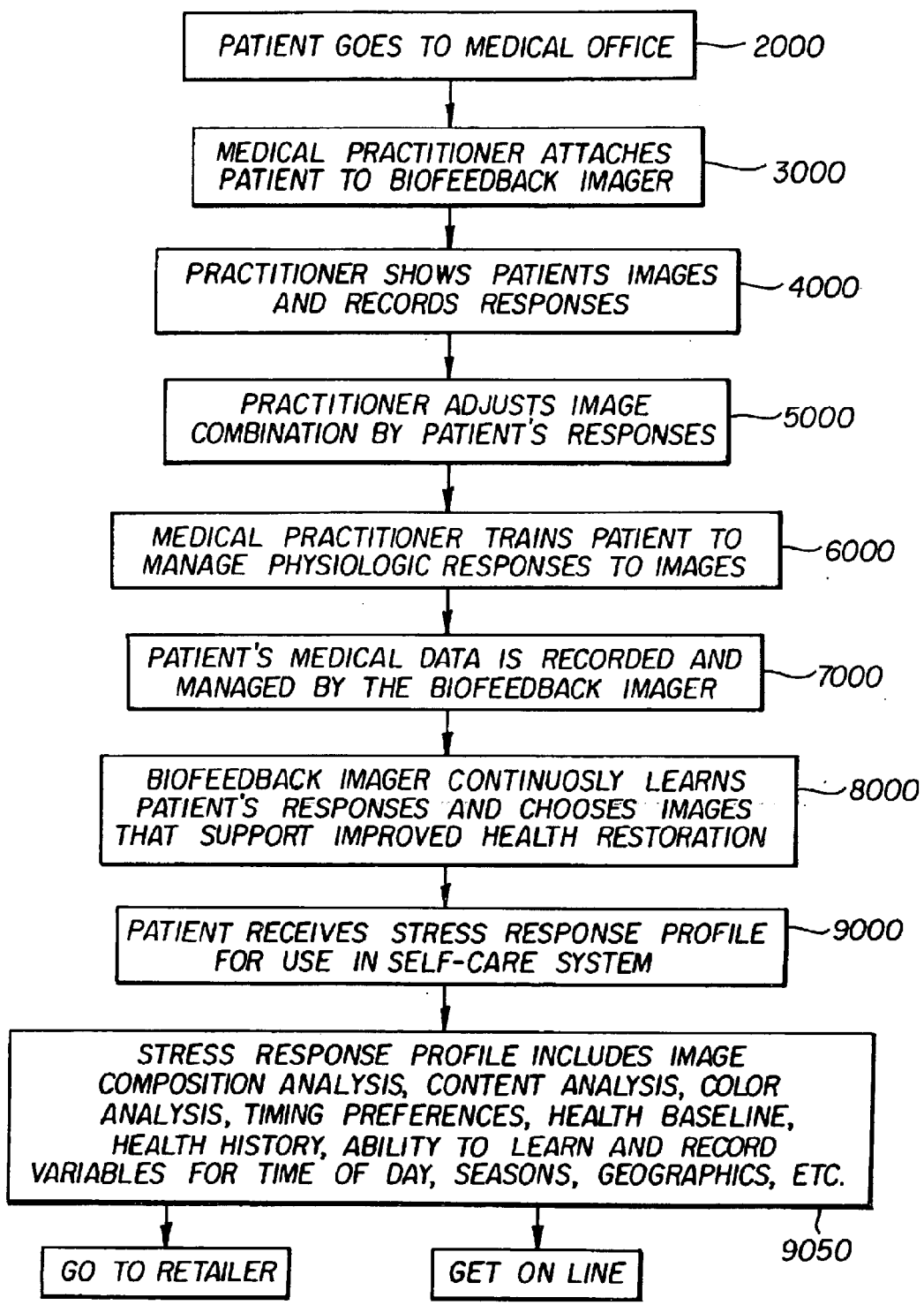
FIG. 7 is a flow chart of an alternative system of the present invention.

In a further aspect of the present invention, as shown by the flow chart of FIG. 7, subject 12 can visit a medical office (step 2000) to control stress using the present invention. As illustrated in FIG. 7, a medical practitioner seats the patient as subject 12 in adaptive autostereoscopic display system 10 (step 3000) as shown in FIG. 1. The practitioner then controls adaptive autostereoscopic display system 10 to display images to subject 12 and records responses to these images (step 4000). It is noted that adaptive autostereoscopic display system 10 is further capable of interfacing with existing biofeedback equipment. Thereafter, the practitioner or control software adjusts the image combination in view of the responses of subject 12 (step 5000). Next, the practitioner trains subject 12 to manage physiological responses to images (step 6000). The medical data for subject 12 is then recorded and managed by adaptive autostereoscopic display system 10 (step 7000). Control logic in adaptive autostereoscopic display system 10 then continuously learns the responses of subject 12 as it builds the personalized preferred image response profile and chooses images that support improved health restoration (step 8000). Subject 12 can thereafter receive a personalized preferred image response profile for use in a self-care system (step 9000).

Image composition analysis can be used to help in building an image response profile, based on the attributes shown in FIG. 6. The profile can also be influenced by color analysis, timing preference, health baseline, health history, ability to learn and record variables for time of day, seasons, geographics, personal or family images, for example. (step 9050). Having the personalized preferred image response profile created by a medical practitioner, subject 12 can now go to a retailer or use an on-line remote connection, adapting the sequence described in the flow chart of FIG. 7 to obtain images that help manage stress.

In this way, the method and apparatus of the present invention overcomes the disadvantage of generalized image selection. Rather than presenting subject 12 with images statistically chosen on the bases of the effects these images had on a large sample of individuals, the images are linked to personal responses. Subject 12 uses the personalized images in a device that uses images or feedback controlled image properties as a biofeedback mechanism for achieving an improved psychological state.

It is recognized that in addition to managing stress, this method and apparatus can also be used as a tool to motivate, teach, focus, or visualize. In addition, adaptive autostereoscopic display system 10 could also be used for entertainment purposes. By measuring physiological response, the display of images or of an image sequence could be selectively adapted in order to obtain a desired type of response from subject 12. Thus, for example, an adventure ride sequence could be speeded up, slowed down, or otherwise adapted to suit the response of each particular subject 12.

The method and apparatus of the present invention also permits the use of a personalized preferred image response profile to allow subject 12 to choose images or a sequence of images from a number of different categories of images such as seascapes, desert scenes, forest scenes, other nature scenes, personal images, or computer-generated images according to data in the personalized preferred image response profile.

The personalized preferred image response profile can also be used for pre-selection, thereby preventing subject 12 from having to choose images or sets of images from a large library of images. The images are selected by comparing the attributes of the images to the personalized preferred image response profile.

The method and apparatus of the present invention also permits subject 12 to use the personalized preferred image response profile to sort, compare, select and keep track of images. With the method and apparatus of the present invention, it is also possible to generate a chart or record of stress levels for periods of time which can be shared, for example, with physicians as part of a diagnostic exercise or treatment plan.

The method and apparatus of the present invention also provides for a device which can be utilized to manage stress and at the same time is portable enough so that it can be used at home, at work, or while traveling.

Although primarily intended for image presentation, adaptive autostereoscopic display system 10 is not limited to the use of images for creating a personalized preferred response profile and helping subject 12 to manage stress. As previously discussed, additional stimuli such as sound, smell, touch, or vibration, could also be used, alone or with images, as a basis for creating the personalized preferred response profile and helping subject 12 to manage stress.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, adaptive autostereoscopic display system 10 could be used in other medical, therapeutic, or entertainment applications. Additional types of feedback sensors could be employed to provide any of the more sophisticated sensing functions known in the virtual reality presentation arts, such as head-tracking or gaze-tracking, for example.

Thus, what is provided is an autostereoscopic display system adapted for psychological health management and to a method for using an autostereoscopic display system for conditioning the psychological state of a subject for biofeedback, stress management, behavior modification, entertainment, and similar applications.

| PARTS LIST | |
|---|---|
| 10 | Adaptive autostereoscopic display system |
| 11 | Detector device |
| 12 | Subject |
| 13 | Interconnect cable |
| 14 | Viewing pupil |
| 14l | Left viewing pupil |
| 14r | Right viewing pupil |
| 16 | Beamsplitter |
| 17 | Control mechanism |
| 18 | Autostereoscopic image delivery system |
| 20 | Projection apparatus |
| 20l | Left-eye projection apparatus |
| 20r | Right-eye projection apparatus |
| 24 | Curved mirror |
| 30l | Left ball lens assembly |
| 30r | Right ball lens assembly |
| 32. | Adjustable chair |
| 36l | Left viewing pupil forming apparatus |
| 36r | Right viewing pupil forming apparatus |
| 40 | Image generator |
| 42 | Image source |
| 50 | Control logic processor |
| 52 | Observer feedback sensor |
| 54 | Camera |
| 58 | Housing |
| 60 | Projection translation apparatus |
| 60l | Left-eye projection translation apparatus |
| 60r | Right-eye projection translation apparatus |

-continued

PARTS LIST

| | |
|---|---|
| 60b | Beamsplitter positioning apparatus |
| 60m | Mirror positioning apparatus |
| 62 | Speaker system |
| 64 | Speaker |
| 66 | Chair servo mechanism |
| 70 | Audio source |
| 80 | Selector device |
| 81 | Selector button |
| 82 | Selector button |
| 83 | Selector button |
| 84 | Selector button |
| 85 | Connector |
| 86 | Display panel |
| 100 | First set of images |
| 102 | Second set of images |
| 104 | Manual feedback control |
| 300 | Initial step |
| 301A | Step |
| 301B | Step |
| 302 | Step |
| 302A | Step |
| 302B | Step |
| 302B' | Step |
| 302C | Step |
| 302C' | Step |
| 302D | Step |
| 302E | Step |
| 302F | Step |
| 303 | Step |
| 304 | Step |
| 305 | Step |
| 306 | Step |
| 400 | Step |
| 500 | Step |
| 600 | Step |
| 700 | Step |
| 800 | Step |
| 900 | Step |
| 1000 | Step |
| 1010 | Step |
| 1020 | Step |
| 2000 | Step |
| 3000 | Step |
| 4000 | Step |
| 5000 | Step |
| 6000 | Step |
| 7000 | Step |
| 8000 | Step |
| 9000 | Step |
| 9050 | Step |

What is claimed is:

1. A system for conditioning the psychological state of a subject, the system comprising:
   (a) an image display for providing an autostereoscopic image to the subject;
   (b) at least one feedback sensor for providing a physiological measurement from the subject;
   (c) a control logic processor obtaining said physiological measurement from said at least one feedback sensor, and controlling the selection and processing of said autostereoscopic image by said image display based on said physiological measurement; and
   wherein said autostereoscopic image is selected from a personalized preferred image response profile.

2. A system for conditioning the psychological state of a subject according to claim 1 wherein said autostereoscopic image is a virtual image viewable at a right viewing pupil and a left viewing pupil.

3. A system for conditioning the psychological state of a subject according to claim 2 wherein said right viewing pupil is formed as the conjugate image of a ball lens.

4. A system for conditioning the psychological state of a subject according to claim 2 wherein said control logic processor modifies said left eye image and said right eye image in order to adjust the stereoscopic viewing relationship between said left viewing pupil and said right viewing pupil for displaying correct parallax information as the subject moves.

5. A system for conditioning the psychological state of a subject according to claim 1 wherein said response profile, is representatively selected to manage a psychological or physical state of said subject.

6. A system for conditioning the psychological state of a subject according to claim 1 wherein said physiological measurement is selected from a group consisting of EMG, EEG, galvanic skin response, skin temperature, heart rate, blood pressure, eye movement, head movement, and pupil dilation.

7. A system for conditioning the psychological state of a subject according to claim 1 wherein said image display forms said autostereoscopic image using a curved mirror.

8. A system for conditioning the psychological state of a subject according to claim 1 wherein said autostereoscopic image is a motion picture image.

9. A system for conditioning the psychological state of a subject according to claim 1 further comprising an image library accessed by said control logic processor.

10. A system for conditioning the psychological state of a subject according to claim 1 wherein said system dynamically modifies the display of said autostereoscopic image according to said physiological measurement.

11. A system for conditioning the psychological state of a subject according to claim 1 wherein said autostereoscopic image originates from film.

12. A system for conditioning the psychological state of a subject according to claim 1 wherein said autostereoscopic image originates from video.

13. A system for conditioning the psychological state of a subject according to claim 1 wherein said autostereoscopic image originates from a computer.

14. A system for conditioning the psychological state of a subject according to claim 1 wherein said autostereoscopic image originates from a camera.

15. A system for conditioning the psychological state of a subject according to claim 1 wherein said autostereoscopic image originates from a storage medium.

16. A system for conditioning the psychological state of a subject according to claim 1 wherein said at least one feedback sensor comprises a camera.

17. A system for conditioning the psychological state of a subject according to claim 1 wherein said at least one feedback sensor comprises a photosensor.

18. A system for conditioning the psychological state of a subject according to claim 1 wherein said at least one feedback sensor comprises a head tracking apparatus.

19. A system for conditioning the psychological state of a subject according to claim 1 wherein said at least one feedback sensor further comprises a gaze tracking apparatus.

20. A system for conditioning the psychological state of a subject according to claim 1 wherein said at least one feedback sensor is coupled to said subject.

21. A system for conditioning the psychological state of a subject according to claim 1 wherein said feedback data comprises an interocular distance obtained from said subject.

22. A system for conditioning the psychological state of a subject according to claim 1 wherein said feedback data indicates a gesture made by said subject.

23. A system for conditioning the psychological state of a subject according to claim 1 wherein said feedback data comprises a distance dimension.

24. A system for conditioning the psychological state of a subject according to claim 1 further comprising an audio output apparatus for providing sound.

25. A system for conditioning the psychological state of a subject according to claim 1 further comprising a chair for seating the subject.

26. A system for conditioning the psychological state of a subject according to claim 25 wherein said feedback sensor is coupled to said chair.

27. A system for conditioning the psychological state of a subject according to claim 25 wherein said chair is capable of being moved in response to a command from said control logic processor.

28. A system for conditioning the psychological state of a subject according to claim 25 further comprising a servo mechanism coupled to said chair.

29. A system for conditioning the psychological stale of a subject according to claim 1 further comprising a movable platform, said movable platform capable of being moved in response to a command from said control logic processor.

30. A system for conditioning the psychological state of a subject according to claim 1 further comprising a tactile output apparatus.

31. A system for conditioning the psychological state of a subject according to claim 30 wherein said tactile output apparatus directs an air flow to said subject.

32. A system for conditioning the psychological state of a subject according to claim 31 wherein said tactile output apparatus controls temperature of said air flow.

33. A system for conditioning the psychological state of a subject according to claim 1 further comprising an olfactory output apparatus for emitting an odor perceptible to said subject.

34. A system for conditioning the psychological state of a subject according to claim 1 wherein said image display comprises a liquid crystal device.

35. A system for conditioning the psychological state of a subject according to claim 1 wherein said image display comprises a digital micromirror device.

36. A system for conditioning the psychological state of a subject according to claim 1 wherein said image display comprises a laser.

37. A system for conditioning the psychological state of a subject according to claim 1 wherein said image display comprises a grating light valve.

38. A system for conditioning the psychological state of a subject according to claim 1 wherein said image display comprises an OLED.

39. A system for conditioning the psychological state of a subject according to claim 1 wherein said at least one feedback sensor comprises an instrumented glove.

40. A system for conditioning the psychological state of a subject according to claim 1 wherein said control logic processor maintains a response profile for the subject, said response profile conditioned by said physiological measurement.

41. A system for conditioning the psychological state of a subject, the system comprising:
(a) an autostereoscopic image display for providing a virtual image to the subject, said virtual image viewable at a right viewing pupil and a left viewing pupil;
(b) at least one feedback sensor for providing a physiological measurement from the subject; and
(c) a control logic processor obtaining said physiological measurement from said at least one feedback sensor, maintaining a response profile conditioned by said physiological measurement, and controlling the selection and processing of said virtual image by said autostereoscopic image display based on said response profile.

42. A system for conditioning the psychological state of a subject according to claim 41 wherein said physiological measurement is selected from a group consisting of EMG, EEG, galvanic skin response, skin temperature, heart rate, blood pressure, eye movement, head movement, and pupil dilation.

43. A system for conditioning the psychological state of a subject according to claim 41 wherein said right viewing pupil is formed as the conjugate image of a ball lens.

44. A system for conditioning the psychological state of a subject according to claim 41 wherein said autostereoscopic image display from said virtual image using a curved mirror.

45. A system for conditioning the psychological state of a subject according to claim 41 wherein said virtual image is a motion picture image.

46. A system for conditioning the psychological state of a subject according to claim 41 further comprising an image library accessed by said control logic processor.

47. A system for conditioning the psychological state of a subject according to claim 41 wherein said system dynamically modifies the display of said virtual image according to said physiological measurement.

48. A system for conditioning the psychological state of a subject according to claim 41 wherein said virtual image originates from film.

49. A system for conditioning the psychological state of a subject according to claim 41 wherein said virtual image originates from video.

50. A system for conditioning the psychological state of a subject according to claim 41 wherein said virtual image originates from a computer.

51. A system for conditioning the psychological state of a subject according to claim 41 wherein said virtual image originates from a camera.

52. A system for conditioning the psychological state of a subject according to claim 41 wherein said virtual image originates from a storage medium.

53. A system for conditioning the psychological state of a subject according to claim 41 wherein said at least one feedback sensor comprises a camera.

54. A system for conditioning the psychological state of a subject according to claim 41 wherein said at least one feedback sensor comprises a photosensor.

55. A system for conditioning the psychological state of a subject according to claim 41 wherein said at least one feedback sensor comprises a head tracking apparatus.

56. A system for conditioning the psychological state of a subject according to claim 41 wherein said at least one feedback sensor further comprises a gaze tracking apparatus.

57. A system for conditioning the psychological state of a subject according to claim 41 wherein said at least one feedback sensor is coupled to said subject.

58. A system for conditioning the psychological state of a subject according to claim 41 wherein said feedback data comprises an interocular distance obtained from said subject.

59. A system for conditioning the psychological state of a subject according to claim 41 wherein said feedback data indicates a gesture made by said subject.

60. A system for conditioning the psychological state of a subject according to claim 41 wherein said feedback data comprises a distance dimension.

61. A system for conditioning the psychological state of a subject according to claim 41 further comprising an audio output apparatus for providing sound.

62. A system for conditioning the psychological state of a subject according to claim 41 further comprising a chair for seating said subject.

63. A system for conditioning the psychological state of a subject according to claim 62 wherein said feedback sensor is coupled to said chair.

64. A system for conditioning the psychological state of a subject according to claim 62 wherein said chair is capable of being moved in response to a command from said control logic processor.

65. A system for conditioning the psychological state of a subject according to claim 41 further comprising a movable platform, said movable platform capable of being moved in response to a command from said control logic processor.

66. A system for conditioning the psychological state of a subject according to claim 41 further comprising a tactile output apparatus.

67. A system for conditioning the psychological state of a subject according to claim 66 wherein said tactile output apparatus directs an air flow to said subject.

68. A system for conditioning the psychological state of a subject according to claim 67 wherein said tactile output apparatus controls temperature of said air flow.

69. A system for conditioning the psychological state of a subject according to claim 41 further comprising an olfactory output apparatus for emitting an odor perceptible to said subject.

70. A system for conditioning the psychological state of a subject according to claim 41 wherein said control logic processor modifies said left eye image and said right eye image in order to adjust the stereoscopic viewing relationship between said left viewing pupil and said right viewing pupil for displaying correct parallax information as the subject moves.

71. A system for conditioning the psychological state of a subject according to claim 41 wherein said autostereoscopic image display comprises a liquid crystal device.

72. A system for conditioning the psychological state of a subject according to claim 41 wherein said autostereoscopic image display comprises a digital micromirror device.

73. A system for conditioning the psychological state of a subject according to claim 41 wherein said autostereoscopic image display comprises a laser.

74. A system for conditioning the psychological state of a subject according to claim 41 wherein said autostereoscopic image display comprises a grating light valve.

75. A system for conditioning the psychological state of a subject according to claim 41 wherein said autostereoscopic image display comprises an OLED.

76. A system for conditioning the psychological state of a subject according to claim 41 wherein said at least one feedback sensor comprises a speech recognition system.

77. A system for conditioning the psychological state of a subject according to claim 41 wherein said at least one feedback sensor comprises an instrumented glove.

78. A system for conditioning the psychological state of a subject according to claim 41 wherein said response profile is from said physiological measurements obtained from said subject.

79. A system for conditioning the psychological state of a subject according to claim 41 wherein said response profile is from said physiological measurements obtained from a plurality of subjects.

80. A system for conditioning the psychological state of a subject, the system comprising:

(a) a stereoscopic image display for providing a stereoscopic image to the subject;

(b) at least one feedback sensor for providing a physiological measurement from said subject; and (c) a control logic processor obtaining said physiological measurement from said at least one feedback sensor, maintaining, for said subject, a personalized preferred image response profile conditioned by said physiological measurement, and controlling the selection and processing of said stereoscopic image by said stereoscopic image display based on said personalized preferred image response profile.

81. A system for conditioning the psychological state of a subject according to claim 80 wherein said physiological measurement is selected from a group consisting of EMG, EEG, galvanic skin response, skin temperature, heart rate, blood pressure, eye movement, head movement, and pupil dilation.

82. A system for conditioning the psychological state of a subject according to claim 80 wherein said stereoscopic image display forms a virtual image.

83. A system for conditioning the psychological state of a subject according to claim 80 wherein said stereoscopic image is a motion picture image.

84. A system for conditioning the psychological state of a subject according to claim 80 further comprising an image library accessed by said control logic processor.

85. A system for conditioning the psychological state of a subject according to claim 80 wherein said system dynamically modifies the display of said stereoscopic image according to said physiological measurement.

86. A system for conditioning the psychological state of a subject according to claim 80 wherein said stereoscopic image originates from film.

87. A system for conditioning the psychological state of a subject according to claim 80 wherein said stereoscopic image originates from video.

88. A system for conditioning the psychological state of a subject according to claim 80 wherein said stereoscopic image originates from a computer.

89. A system for conditioning the psychological state of a subject according to claim 80 wherein said stereoscopic image originates from a camera.

90. A system for conditioning the psychological state of a subject according to claim 80 wherein said stereoscopic image originates from a storage medium.

91. A system for conditioning the psychological state of a subject according to claim 80 wherein said at least one feedback sensor comprises a camera.

92. A system for conditioning the psychological state of a subject according to claim 80 wherein said at least one feedback sensor comprises a photosensor.

93. A system for conditioning the psychological state of a subject according to claim 80 wherein said at least one feedback sensor comprises a head tracking apparatus.

94. A system for conditioning the psychological state of a subject according to claim 80 wherein said at least one feedback sensor further comprises a gaze tracking apparatus.

95. A system for conditioning the psychological state of a subject according to claim 80 wherein said at least one feedback sensor is coupled to said subject.

96. A system for conditioning the psychological state of a subject according to claim 80 wherein said feedback data comprises an interocular distance obtained from said subject.

97. A system for conditioning the psychological state of a subject according to claim 80 wherein said feedback data indicates a gesture made by said subject.

98. A system for conditioning the psychological state of a subject according to claim 80 wherein said feedback data comprises a distance dimension.

99. A system for conditioning the psychological state of a subject according to claim 80 further comprising an audio output apparatus for providing sound.

100. A system for conditioning the psychological state of a subject according to claim 80 further comprising a chair for seating said subject.

101. A system for conditioning the psychological state of a subject according to claim 100 wherein said feedback sensor is coupled to said chair.

102. A system for conditioning the psychological state of a subject according to claim 100 wherein said chair is capable of being moved in response to a command from said control logic processor.

103. A system for conditioning the psychological state of a subject according to claim 100 further comprising a vibration transducer coupled to said chair.

104. A system for conditioning the psychological state of a subject according to claim 80 further comprising a movable platform, said movable platform capable of being moved in response to a command from said control logic processor.

105. A system for conditioning the psychological state of a subject according to claim 80 further comprising a tactile output apparatus.

106. A system for conditioning the psychological state of a subject according to claim 105 wherein said tactile output apparatus directs an air flow to said subject.

107. A system for conditioning the psychological state of a subject according to claim 106 wherein said tactile output apparatus controls temperature of said air flow.

108. A system for conditioning the psychological state of a subject according to claim 80 further comprising an olfactory output apparatus for emitting an odor perceptible to said subject.

109. A system for conditioning the psychological state of a subject according to claim 80 further comprising a manipulable device for interaction with said subject.

110. A system for conditioning the psychological state of a subject according to claim 80 wherein said stereoscopic image display comprises a liquid crystal device.

111. A system for conditioning the psychological state of a subject according to claim 80 wherein said stereoscopic image display comprises a digital micromirror device.

112. A system for conditioning the psychological state of a subject according to claim 80 wherein said stereoscopic image display comprises a laser.

113. A system for conditioning the psychological state of a subject according to claim 80 wherein said stereoscopic image display comprises a grating light valve.

114. A system for conditioning the psychological state of a subject according to claim 80 wherein said stereoscopic image display comprises an OLED.

115. A system for conditioning the psychological state of a subject according to claim 80 wherein said at least one feedback sensor comprises a speech recognition system.

116. A system for conditioning the psychological state of a subject according to claim 80 wherein said at least one feedback sensor comprises an instrumented glove.

\* \* \* \* \*